US012746228B2

United States Patent
(12) United States Patent
Aguilera et al.

(10) Patent No.: US 12,746,228 B2
(45) Date of Patent: Sep. 29, 2026

(54) TUBULIN POLYMERIZATION INHIBITOR FOR CANCER THERAPY

(71) Applicant: Board of Regents, The University of Texas System, Austin, TX (US)

(72) Inventors: Renato J. Aguilera, El Paso, TX (US); Edgar A. Borrego Puerta, El Paso, TX (US)

(73) Assignee: Board of Regents, The University of Texas System, Austin, TX (US)

(*) Notice: Subject to any disclaimer, the term of this patent is extended or adjusted under 35 U.S.C. 154(b) by 419 days.

(21) Appl. No.: 18/496,111

(22) Filed: Oct. 27, 2023

(65) Prior Publication Data

US 2024/0139157 A1 May 2, 2024

Related U.S. Application Data

(60) Provisional application No. 63/381,313, filed on Oct. 28, 2022.

(51) Int. Cl.
*A61K 31/4192* (2006.01)

(52) U.S. Cl.
CPC ................................ *A61K 31/4192* (2013.01)

(58) Field of Classification Search
CPC ................................................. A61K 31/4192
See application file for complete search history.

(56) References Cited

FOREIGN PATENT DOCUMENTS

WO WO-2022086079 A1 * 4/2022 ......... A61K 31/4184

OTHER PUBLICATIONS

Yan et al. "Synthesis, Evaluation, and Mechanism Study of Novel Indole-Chalcone Derivatives Exerting Effective Antitumor Activity Through Microtubule Destabilization in Vitro and in Vivo", J. Med. Chem. 2016, 59, 5264-5283 (Year: 2016).*
Cui et al. "SAR Investigation and Discovery of Water-Soluble 1-Methyl-1,4-dihydroindeno[1,2-c] pyrazoles as Potent Tubulin Polymerization Inhibitors" J. Med. Chem. 2020, 63, 14840-14866 (Year: 2020).*
American Chemical Society. Chemical Abstract Service, RN#: 1185699-58-4. Entered into STN: Sep. 18, 2009. (Year: 2009).*
Borrego et al. "A Novel Pyrazole Exhibits Potent Anticancer Cytotoxicity via Apoptosis, Cell Cycle Arrest, and the Inhibition of Tubulin Polymerization in Triple-Negative Breast Cancer Cells", Cells 2024, 13, 1225. (Year: 2024).*
Anichina, et al., "1H-benzimidazole-2-yl hydrazones as tubulin-targeting agents: Synthesis, structural characterization, anthelmintic activity and antiproliferative activity against MCF-7 breast carcinoma cells and molecular docking studies," Chemico-Biological Interactions, Jun. 15, 2021, 14 pages, Elsevier, accessed Oct. 27, 2023, https://doi.org/10.1016/j.cbi.2021.109540.
Guitierrez, et al., "A new pyridazinone exhibits potent cytotoxicity on human cancer cells via apoptosis and poly-ubiquitinated protein accumulation," Cell Biol Toxicol, Dec. 2019, 27 pages, HHS Public Access, accessed Oct. 27, 2023, doi:10.1007/s10565-019-09466-8.
Gutierrez, et al., "Identification of a Potent Cytotoxic Pyrazole with Anti-Breast Cancer Activity That Alters Multiple Pathways," Cells, Jan. 12, 2022, 32 pages, MDPI, accessed Oct. 27, 2023, https://doi.org/10.3390/cells11020254.
Ibrahim, et al., "Potent Quinoline-Containing Combretastatin A-4 Analogues: Design, Synthesis, Antiproliferative, and Anti-Tubulin Activity," Pharmaceuticals, Nov. 15, 2020, 23 pages, MDPI, Basel, Switzerland, accessed Oct. 27, 2023, http://dx.doi.org/10.3390/ph13110393.
Janicke, et al., "Caspase-3 Is Required for DNA Fragmentation and Morphological Changes Associated with Apoptosis," The Journal of Biological Chemistry, Apr. 17, 1998, pp. 9357-9360, vol. 273, No. 16, The American Society for Biochemistry and Molecular Biology, Inc., accessed Oct. 27, 2023, https://pubmed.ncbi.nlm.nih.gov/9545256/.
Kumar, "Caspase function in programmed cell death," Cell Death and Differentiation, Copyright 2007, pp. 32-43, vol. 14, Nature Publishing Group, accessed Oct. 27, 2023, https://www.nature.com/articles/4402060.
Lema, et al., "Differential nuclear staining assay for high-throughput screening to identify cytotoxic compounds," Curr Cell Biochem, Mar. 31, 2016, 23 pages, HHS Public Access, accessed Oct. 27, 2023, https://www.ncbi.nlm.nih.gov/pmc/articles/PMC4816492/.
Smith, et al., "Etoposide-induced cell cycle delay and arrest-dependent modulation of DNA topoisomerase H in small-cell lung cancer cells," Br. J. Cancer, Jul. 4, 1994, pp. 914-921, Macmillan Press Ltd., accessed Oct. 27, 2023, doi: 10.1038/bjc.1994.420.
Van Engeland, et al., "Annexin V-Affinity Assay:a Review on an Apoptosis Detection System Based on Phosphatidylserine Exposure," Cytometry 31, Copyright 1998, 9 pages, Wiley Online Library, accessed Oct. 27, 2023, https://onlinelibrary.wiley.com/doi/pdf/10.1002/%28SICI%291097-0320%2819980101%2931%3A1%3C1%3A%3AAID-CYTO1%3E3.0.CO%3B2-R.
Varela-Ramirez, et al., "Cytotoxic effects of two organotin compounds and their mode of inflicting cell death on four mammalian cancer cells," Cell Biol Toxicol, Jun. 2001, 15 pages, NIH Public Access, accessed Oct. 27, 2023, doi:10.1007/s10565-010-9178-y.
Villanueva, et al., "The Antimalarial Drug Pyronaridine Inhibits Topoisomerasell in Breast Cancer Cells and Hinders Tumor Progression In Vivo," Clin Cancer Drugs, Mar. 2021, vol. 8, pp. 50-56, accessed Oct. 27, 2023.
Wang, et al., "Prediction of Drug-Target Interactions for Drug Repositioning Only Based on Genomic Expression Similarity," PLOS Computational Biology, Nov. 2013, 9 pages, vol. 9, Issue 11, accessed Oct. 27, 2023, doi:10.1371/journal.pcbi.1003315.

* cited by examiner

*Primary Examiner* — John S Kenyon
*Assistant Examiner* — Bin Tao
(74) *Attorney, Agent, or Firm* — Yee & Associates, P.C.

(57) ABSTRACT

Provided herein is a compound and method for treating cancer cells. The method comprises administering cancer cells with a compound having the chemical structure of 2-{4-[4-methoxy-3-(trifluoromethyl)phenyl]-1H-pyrazol-1-yl}-N-(2-methyl-2H-1,2,3-triazol-4-yl)acetamide to induce apoptosis of the cancer cells and inhibit tubulin polymerization.

2 Claims, 11 Drawing Sheets

200

| TISSUE/CELL TYPE (202) | CELL LINE (204) | $CC_{50}$ (206) | SCI | EXPOSURE TIME (208) |
|---|---|---|---|---|
| TRIPLE-NEGATIVE BREAST CANCER | MDA-MB-231 | 0.93 μM | 19.26 | 72 H |
| BREAST ADENOCARCINOMA | MCF7 | 0.23 μM | 77.91 | 72 H |
| DUCTAL BREAST CARCINOMA | HCC 70 | 0.74 μM | 24.21 | 72 H |
| DUCTAL BREAST CARCINOMA | T47D | 0.63 μM | 28.44 | 72 H |
| BREAST NORMAL | MCF10A | 4.40 μM | N/A | 72 H |
| MELANOMA | A375 | 0.34 μM | 52.70 | 72 H |
| COLON CANCER | HT-29 | 0.47 μM | 38.12 | 72 H |
| COLON CANCER | COLO 205 | 0.30 μM | 59.73 | 72 H |
| LUNG CANCER | A549 | 0.17 μM | 105.41 | 72 H |
| LIVER CANCER | HepG2 | 0.36 μM | 49.77 | 72 H |
| PANCREATIC CANCER | PANC-1 | 0.28 μM | 64 | 72 H |
| PROSTATE CANCER | PC3 | 0.92 μM | 19.47 | 72 H |
| NORMAL FIBROBLAST | HS27 | 17.92 μM | N/A | 72 H |
| ACUTE LYMPHOBLASTIC LEUKEMIA | CEM | 0.42 μM | 42.66* | 48 H |
| ACUTE LYMPHOBLASTIC LEUKEMIA | NALM6 | 2.07 μM | 8.65* | 48 H |
| ACUTE PROMYELOCYTIC LEUKEMIA | HL-60 | 0.82 μM | 21.85* | 48 H |
| BURKITT'S LYMPHOMA | RAMOS | 0.75 μM | 23.89* | 48 H |
| ACUTE T CELL LEUKEMIA | JURKAT | 0.32 μM | 56* | 48 H |
| CHRONIC MYELOID LEUKEMIA | KCL22 | 0.72 μM | 24.88* | 48 H |

** SCI WAS CALCULATED WITH HS27 AT 72 HOURS*

FIG. 2

600

| UPREGULATED GENES | | | DOWNREGULATED GENES | | |
|---|---|---|---|---|---|
| ADAMTS1 | IL24 | RGMB-AS1 | ADAMTS15 | ID1 | SMAD6 |
| ADAMTS6 | ITGB3 | S1PR1 | ADORA1 | ID3 | SYT2 |
| AKAP12 | KISS1 | SEMA7A | APOL3 | IFIT1 | TMEM37 |
| ALS2CL | KRTAP2-1 | SERPINB2 | APOL6 | IFIT2 | TCS22D3 |
| ARHGAP22 | KRTAP2-3 | SERPINB1 | ATH3 | IFIT3 | VIPR1 |
| C1orf110 | LAMA1 | SH3BP5L | ATOH8 | KLRK1 | ZC3H12D |
| CALD1 | LCP1 | SH3RF2 | BCL3 | LINC01085 | ZFP36 |
| CD177 | LINC00702 | SLC20A2 | BMF | LOC100506895 | |
| CD274 | LINC00704 | SMTN | BMP4 | LOC284454 | |
| CREB5 | LOC152225 | SOCS2 | CIITA | MAP2K6 | |
| DDR2 | NAV3 | SPHK1 | CMKLR1 | METTL7A | |
| DUSP8 | NEDD4L | SPOCD1 | CSRNP3 | OASL | |
| ETS1 | NLRP3 | TAGLN | CX3CL1 | OSR2 | |
| FGF1 | PDZD2 | TMEM171 | CXCL10 | PARD6B | |
| FGF5 | PLAT | TNFSF15 | CXXC4 | PCDH18 | |
| FHL2 | PLAUR | TRPC4 | CYP1B1 | PDE4B | |
| GLIPR1 | PLXNA2 | UBASH3B | DBP | PDE7B | |
| HAS2 | PROSER2 | VCAN | EGR1 | PIK3C2B | |
| HAS2-AS1 | PTPRR | ZNF804A | FOS | PLEKHS1 | |
| HBEGF | RELN | | FOSB | SLCO4C1 | |
| IL1A | RGMB | | GGT3P | SLITRK5 | |

FIG. 6

700

702

704

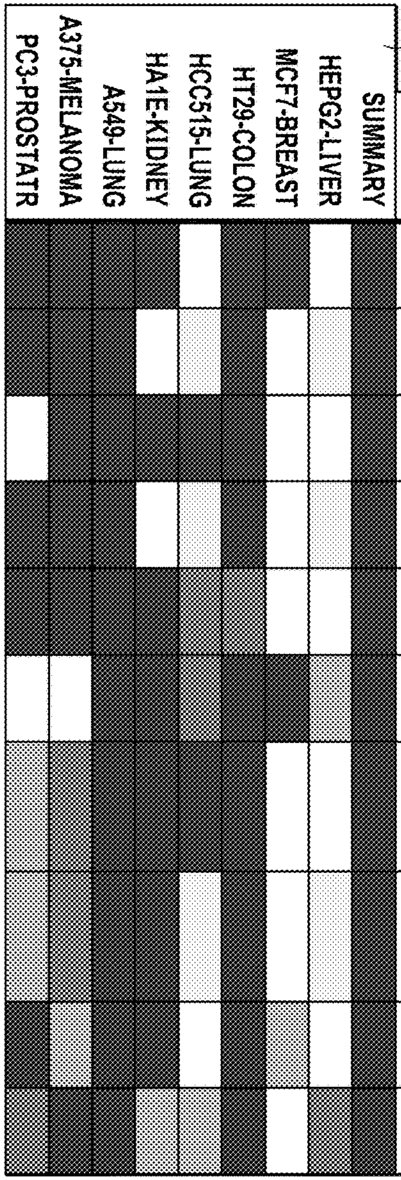

| # | MEDIAN TAU SCORE | NAME | DESCRIPTION | TYPE OF INHIBITOR |
|---|---|---|---|---|
| 1 | 99.12 | NOCODAZOLE | TUBULIN INHIBITOR, TUBULIN POLYMERIZATION INHIBITOR | TUBULIN INHIBITOR |
| 2 | 99.04 | VINDESINE | TUBULIN INHIBITOR, MICROTUBULE INHIBITOR, VINCA ALKALOID | TUBULIN INHIBITOR |
| 3 | 98.97 | ALBENDAZOLE | TUBULIN INHIBITOR, ACETYLCHOLINESTERASE INHIBITOR, MICROTUBULE INHIBITOR | TUBULIN INHIBITOR |
| 4 | 98.48 | FLUBENDAZOLE | ACETYLCHOLINESTERASE INHIBITOR, MICROTUBULE INHIBITOR, TUBULIN INHIBITOR | TUBULIN INHIBITOR |
| 5 | 97.90 | VINBLASTINE | MICROTUBULE FORMATION INHIBITOR, TUBULIN INHIBITOR, TUBULIN POLYMERIZATION INHIBITOR | TUBULIN INHIBITOR |
| 6 | 97.85 | OXIBENDAZOLE | DNA POLYMERASE INHIBITOR, TUBULIN INHIBITOR | TUBULIN INHIBITOR |
| 7 | 97.71 | ABT-751 | TUBULIN INHIBITOR, DIHYDROPTEROATE SYNTHASE, MICROTUBULE INHIBITOR, PABA ANTAGONIST, TUBULIN POLYMERIZATION INHIBITOR | TUBULIN INHIBITOR |
| 8 | 97.56 | VINCRISTINE | TUBULIN INHIBITOR, MICROTUBULE INHIBITOR, MICROTUBULE POLYMERIZATION INHIBITOR, TUBULIN POLYMERIZATION INHIBITOR, VINCA ALKALOID | TUBULIN INHIBITOR |
| 9 | 96.03 | SA-792574 | MICROTUBULE INHIBITOR, TUBULIN INHIBITOR | TUBULIN INHIBITOR |
| 10 | 96.55 | SA-63133 | CASEIN KINASE INHIBITOR, TUBULIN INHIBITOR | TUBULIN INHIBITOR |

FIG. 7

TUBULIN POLYMERIZATION INHIBITOR FOR CANCER THERAPY

CROSS-REFERENCE TO RELATED APPLICATION

This application claims the benefit of U.S. Provisional Patent Application Ser. No. 63/381,313, filed Oct. 28, 2022, and entitled "Discovery of a Novel Tubulin Polymerization Inhibitor as an Anticancer Agent;" which is incorporated herein by reference in its entirety.

STATEMENT OF GOVERNMENT INTERESTS

This invention was made with government support under R16 GM149379 awarded by the National Institutes of Health. The government has certain rights in the invention.

BACKGROUND

1. Field

The disclosure relates generally to tubulin polymerization inhibitor and more specifically to a novel tubulin polymerization inhibitor for cancer therapy.

2. Description of the Related Art

Cancer is a complex group of diseases characterized by uncontrolled growth and division of cells within the body. The development of cancer involves a series of genetic mutations and cellular changes that disrupt the normal regulation of cell division and survival. In other words, cancer development is linked to genetic mutations and cellular processes that result in the loss of normal control over cell proliferation and survival.

The initiation of cancer usually begins with genetic mutations. The alterations in genes can occur spontaneously due to environmental factors such as radiation and chemical exposure. In addition, genetic mutations can be a result of inherited genetic predispositions. In this case, genetic mutations can affect genes that control cell cycle progression, DNA repair, and apoptosis (i.e., cell death).

As a result, mutated genes that regulate cell division may become permanently turned on, thereby driving cells to divide and proliferate uncontrollably. On the other hand, mutations in tumor suppressor genes that inhibit cell division and promote apoptosis can become inactivated, further contributing to uncontrolled growth of tumor cells.

SUMMARY

The illustrative embodiments provide a compound and method for treating cancer cells. The method comprises administering cancer cells with a compound having the chemical structure of 2-{4-[4-methoxy-3-(trifluoromethyl) phenyl]-1H-pyrazol-1-yl}-N-(2-methyl-2H-1,2,3-triazol-4-yl)acetamide to induce apoptosis of the cancer cells and inhibit tubulin polymerization.

Other objects, features and advantages of the present disclosure will become apparent from the following detailed description.

BRIEF DESCRIPTION OF THE DRAWINGS

FIG. 2 illustrates a table for evaluating cytotoxicity of PTA-1 on different cell lines in accordance with an illustrative embodiment;

FIG. 6 depicts a table of genes regulated by PTA-1 in accordance with an illustrative embodiment;

FIG. 7 illustrates a connectivity map of known cancer drugs;

DETAILED DESCRIPTION

The illustrative embodiments recognize and take into account a number of different considerations as described herein. For example, the illustrative embodiments recognize and take into account that irregular cell division that includes mitosis and meiosis contribute to cancer cell development.

The illustrative embodiments also recognize and take into account that cancer cells can develop resistance to chemotherapy and radiation therapies from acquisition of additional mutations, changes in gene expression, or the activation of alternative signaling pathways.

The illustrative embodiments also recognize and take into account that microtubules play important roles in cell division, intracellular transport, and maintenance of cell shape. The illustrative embodiments also recognize and take into account that constant assembly and disassembly of tubulin subunits are vital for the process described above.

As used herein, when used with reference to items, "a number of" means one or more of the items. For example, "a number of different types of communication networks" is one or more different types of communication networks. Similarly, "a set of," when used with reference to items, means one or more of the items.

Further, the term "at least one of," when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

For example, without limitation, "at least one of item A, item B, or item C" may include item A, item A and item B, or item B. This example may also include item A, item B, and item C or item B and item C. Of course, any combination of these items may be present. In some illustrative examples, "at least one of" may be, for example, without limitation, two of item A; one of item B; and ten of item C; four of item B and seven of item C; or other suitable combinations.

Figure 1:
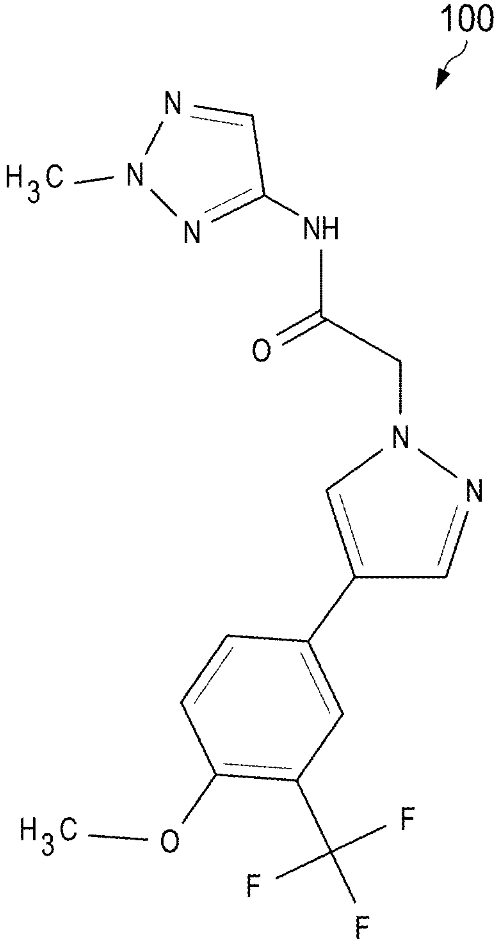
FIG. 1 illustrates a chemical structure for a tubulin polymerization inhibitor in accordance with an illustrative embodiment.

With reference now to the figures, and in particular, with reference to FIG. 1, an illustration of a chemical structure for a tubulin polymerization inhibitor is depicted in accordance with an illustrative embodiment. In this illustrative example, chemical structure 100 illustrates the chemical structure for 2-{4-[4-methoxy-3-(trifluoromethyl)phenyl]-1H-pyrazol-1-yl}-N-(2-methyl-2H-1,2,3-triazol-4-yl)acetamide (PTA-1). In this illustrative example, PTA-1 can be used as a tubulin polymerization inhibitor for cancer therapy.

In this illustrative example, tubulin polymerization inhibitor is a class of drugs used in cancer chemotherapy for interfering with the normal assembly of microtubules in cancer cells. Tubulin polymerization inhibitors can stabilize microtubules by preventing addition of tubulin subunits or promote microtubule polymerization that leads to the disassembly of microtubules. In this example, the disruption to microtubule assembly has great impact on cell division as microtubules are crucial for forming mitotic spindles that separate chromosomes during cell division. In other words, tubulin polymerization inhibitors can disrupt the progression of cell cycle and prevent cancer cells from dividing and proliferating.

In this illustrative example, PTA-1 can be identified through compound screening by performing differential nuclear staining assay on acute lymphoblastic leukemia CEM T-cell line. Differential nuclear staining assay measures cell viability using Hoechst 33342 fluorescent stain and propidium iodide dyes that stain all nuclei and dead cell nuclei.

With reference now to FIG. 2, a table for evaluating cytotoxicity of PTA-1 on different cell lines is depicted in accordance with an illustrative embodiment. In FIG. 2, PTA-1 with chemical structure 100 shown in FIG. 1 is tested to determine cytotoxic activities of PTA-1 on different cell lines.

In table 200, column 202 indicates the type of cells that are used to test cytotoxic activities of PTA-1, column 204 indicates the cell line used to test cytotoxic activities of PTA-1, column 206 indicates the $CC_{50}$ values for different cell lines, and column 208 indicates the length of time that different cell lines are exposed to PTA-1. $CC_{50}$ (50% cytotoxic concentration) values are the concentration of PTA-1 at which 50% of tested cells exhibit cell death or loss of viability. In this illustrative example, a lower $CC_{50}$ value for a cell line indicates a higher level of PTA-1 cytotoxicity, meaning that PTA-1 is more toxic to the cell line.

As depicted, the most sensitive cancer cell line for lymphomas is the sample from Jurkat cell line, where PTA-1 has a $CC_{50}$ value of 0.32 μM. In other words, 0.32 μM of PTA-1 can cause 50% of cells in sample from the Jurkat cell line to exhibit cell death or loss of viability. In this illustrative example, A549 cell line for lung cancer is the most sensitive to PTA-1 among all cancerous cell line and MDA-MB-231 is the least sensitive to PTA-1 among all cancerous cell line. In contrast, the two non-cancerous cell lines (i.e., MCF10A cell line and HS27 cell line) exhibit significantly lower sensitivity towards PTA-1. In FIG. 2, the significant difference in $CC_{50}$ values between cancerous cell lines and non-cancerous cell lines indicates that PTA-1 can be used as anticancer agent without harming the normal cells in human body.

In this illustrative example, the selective cytotoxicity index value is used to determine if a compound has activity preferentially toward cancer cells. In other words, the selective cytotoxicity index value can be used to determine if a compound demonstrates a higher degree of effectiveness or selectivity in inhibiting the growth or promoting the death of cancer cells. The selective cytotoxicity index (SCI) value is calculated by dividing the $CC_{50}$ of the compound in non-cancerous cells (HS27 human fibroblasts or MCF-10A breast epithelial cells) by the $CC_{50}$ in cancer cells. A compound is especially active in cancer cells if the SCI of the compound is ≥1. In this example, PTA-1 has selectivity towards MDA-MB-231 than to MCF10A cells with an SCI value of 4.73. Therefore, the MDA-MB-231 cell line is chosen for further studies. As can be seen in FIG. 2, the SCI values ranged from 8.65 on ALL cell line NALM6 to 105 in the lung cancer cell line A549; thus, indicating strong selectivity against cancer cells.

Figure 3:
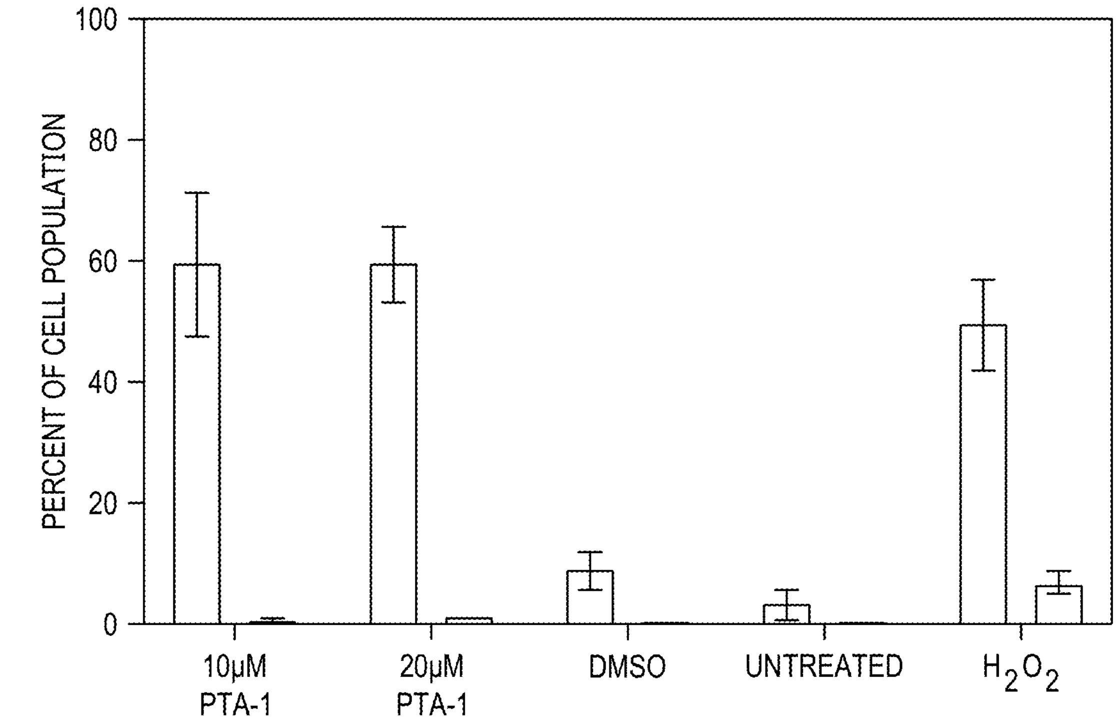
FIG. 3 shows the percentage of cells that undergo PTA-1 induced apoptosis by measuring phosphatidylserine externalization of cells in accordance with an illustrative embodiment.

FIG. 3 shows the percentage of cells that undergo PTA-1 induced apoptosis by measuring phosphatidylserine externalization of cells in accordance with an illustrative embodiment. Phosphatidylserine externalization is a cellular process that involves the translocation of phosphatidylserine from the inner leaflet of the cell's plasma membrane to the outer leaflet. The externalization of phosphatidylserine is recognized by other cells as a signal for engulfment and removal without causing inflammation or damage.

The plot illustrated in FIG. 3 was generated by Annexin V assay analyzed by flow cytometry showing the externalization of the phospholipid phosphatidylserine (PS). Treatment of MDA-MB-231 cells with PTA-1 at concentrations of 10 μM and 20 μM for 24 hours induces apoptosis as shown by PS externalization. Each bar represents the average of at least three technical replicates.

As shown in FIG. 3, PTA-1 at a concentration of 10 μM and 20 μM for 24 hours induces the externalization of phosphatidylserine in 59.4% and 59.7% of the MDA-MB-231 cell population, respectively. Dimethylsulfoxide (DMSO) treatment induced the externalization of the phosphatidylserine in 9% of the cell population. Additionally, the positive control of $H_2O_2$ induces phosphatidylserine externalization in 49.9% of the cell population. Furthermore, in untreated cells, just 3.4% of the cell population experiences phosphatidylserine externalization. FIG. 3 clearly shows that different concentrations of PTA-1 can induce phosphatidylserine externalization at a significantly higher rate compared to controls, therefore indicating that PTA-1 induces the externalization of PS and apoptosis for MDA-MB-231 cells.

Figure 4:
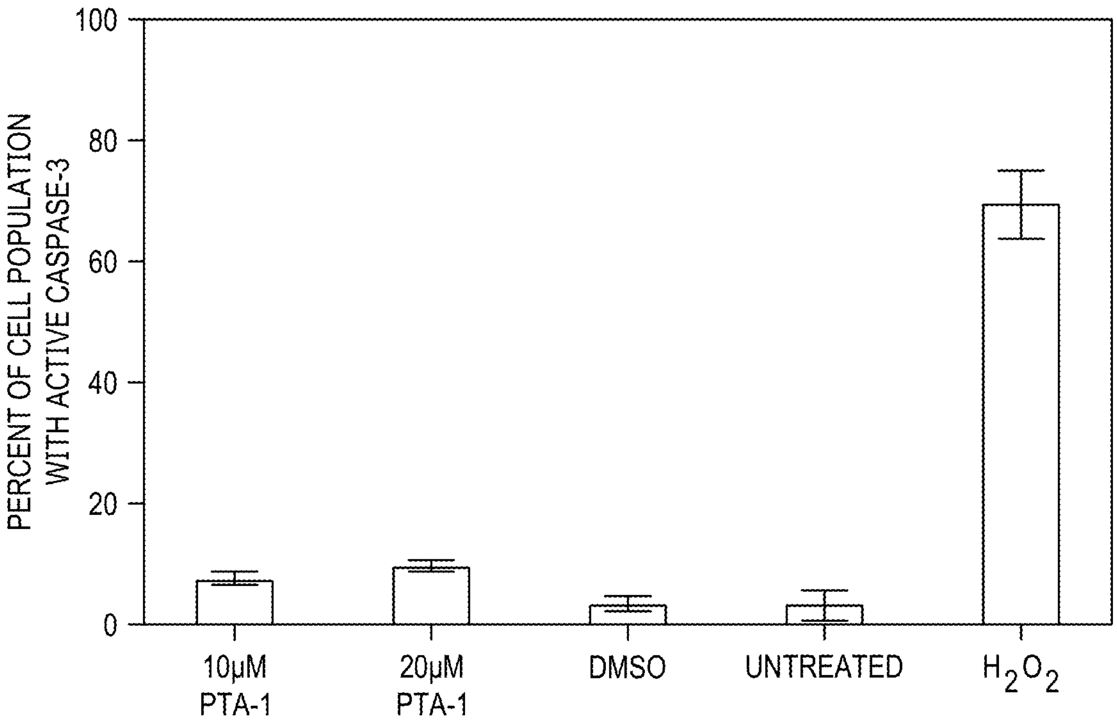
FIG. 4 depicts a plot illustrating PTA-1 induced caspase-3 activation in accordance with an illustrative embodiment.

FIG. 4 depicts a plot illustrating PTA-1 induced caspase-3 activation in accordance with an illustrative embodiment. In FIG. 4, the induction of apoptosis from PTA-1 is corroborated by detecting the activation of the enzyme caspase-3. The fluorogenic reagent NucView 488 caspase-3 substrate was used to detect the activation of caspase 3 via flow cytometry. MDA-MB-231 cells treated with 10 μM and 20 μM of PTA-1 compound significantly induced the activation of Caspase 3, corroborating apoptosis as the cell death mechanism exerted by PTA-1. The average of 3 replicates is represented by each bar.

Caspase enzymes are activated during apoptosis and eventually result in DNA cleavage. In this example, caspase-3 is activated after exposure of the MDA-MB-231 cells at a concentration of 10 μM and 20 μM of PTA-1. In contrast, the controls with untreated cells and treatment using DMSO did not activate caspase-3. The data shown in FIG. 4 corroborate the induction of apoptosis as the mechanism of cell death.

FIGS. 5A-5D illustrate plots demonstrating PTA-1 induced arrest in different phases of cell cycle in accordance with an illustrative embodiment. FIGS. 5A-5D show the percentages of cells that are affected in different phase after treatment of PTA-1.

Cell cycle is a highly regulated process that allows cells to grow, replicate, and divide into two daughter cells. The cycle consists of several phases with specific functions. For example, the G1 phase is the first phase of the cell cycle that follows cell division and is a period for cell growth. During G1 phase, the cell prepares to replicate its DNA and synthesizes various molecules needed for DNA replication.

The next phase in the cell cycle is the S phase. In the S phase, DNA replication occurs by duplicating genetic material from the cell to create two complete sets of DNA. The S phase ensures that each daughter cell has a complete set of genetic information. The G2 phase follows DNA synthesis in the S phase and is a second period for cell growth. During G2 phase, the cell prepares for mitosis or meiosis by synthesizing additional proteins and organelles necessary for cell division. Lastly, the M phase is the phase of cell division. The M phase has several stages for the cell's chromosomes to condense, align, and separate to produce two daughter cells (in mitosis) or four daughter cells (in meiosis).

Figure 5A:
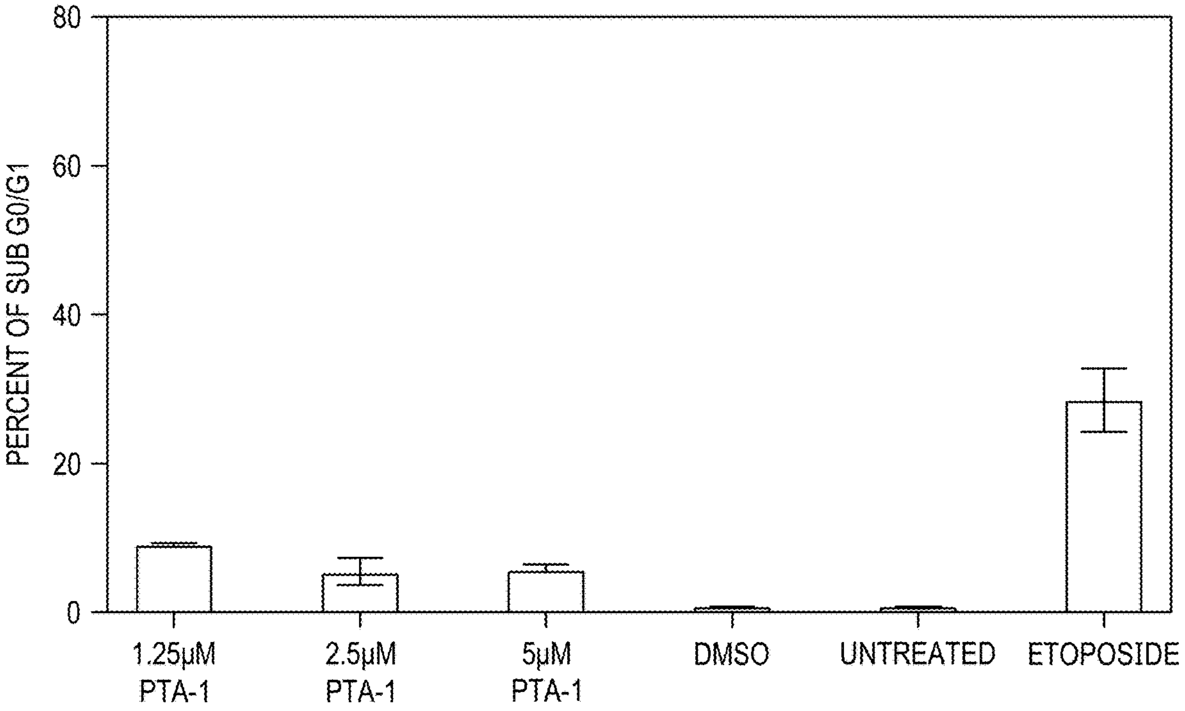
FIG. 5A illustrates PTA-1 induced DNA Fragmentation of cells in the sub G0/G1 phase in accordance with an illustrative embodiment.

FIGS. 5A-5D illustrate how PTA-1 alters the progression of the MDA-MB-231 cell cycle. Etoposide is used as a positive control. FIG. 5A illustrates PTA-1 induced DNA fragmentation as denoted in the sub G0/G1 phase. As shown in FIG. 5A, etoposide causes DNA fragmentations in 28.6% of the cells. In contrast, cells treated with DMSO at concentration of 0.1% shows 0.41% of the cells are in the sub G0/G1 phase, and 0.59% of untreated cells are observed in the sub G0/G1 phase. In this example, cells treated with PTA-1 with concentrations of 1.25 μM, 2.5 μM, and 5 μM shows significantly higher rates of DNA fragmentations compared to cells treated with DMSO and untreated cells. Such observation indicates that PTA-1 causes the fragmentation of the DNA in cells in the sub G0/G1 phase.

Figure 5B:
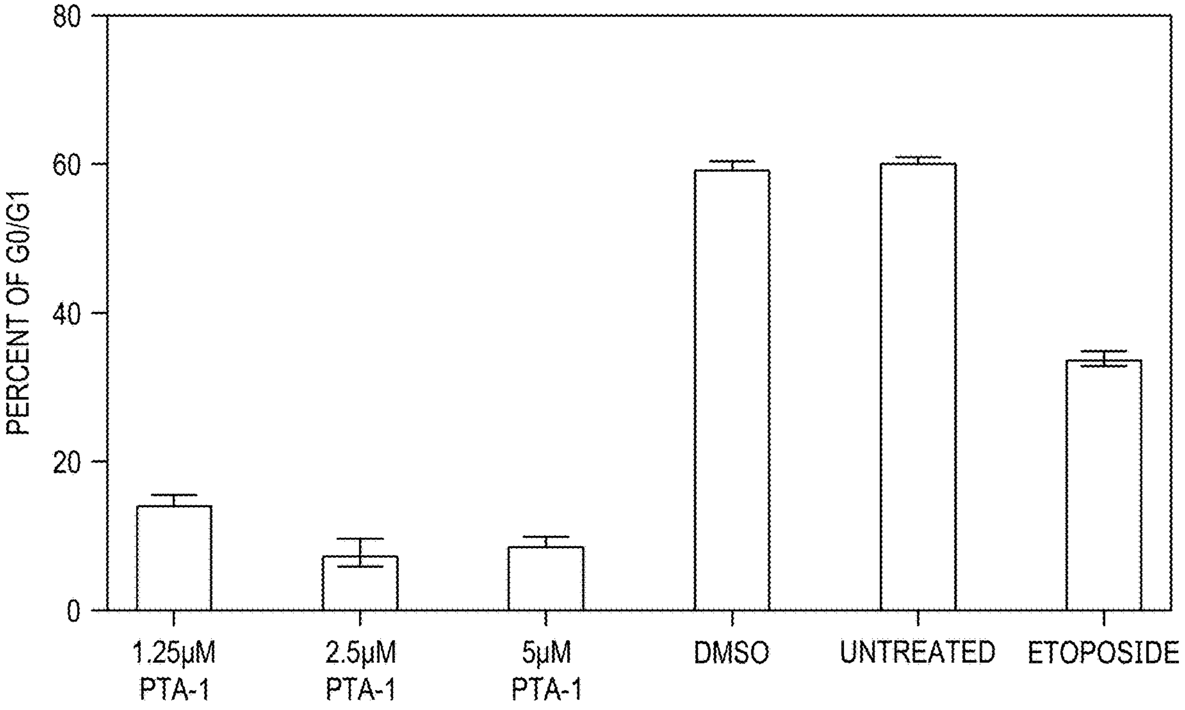
FIG. 5B illustrates PTA-1 did not induce arrest of cells in the G0/G1 phase in accordance with an illustrative embodiment.

As depicted in FIG. 5B, PTA-1 at different concentrations did not result in a higher percentage of cells in the G0/G1 phase. In this example, FIG. 5B indicates that PTA-1 does not arrest cells at the G0/G1 phase. An arrest of cell refers to a halt the progression and development of cells in cell cycle.

Figure 5C:
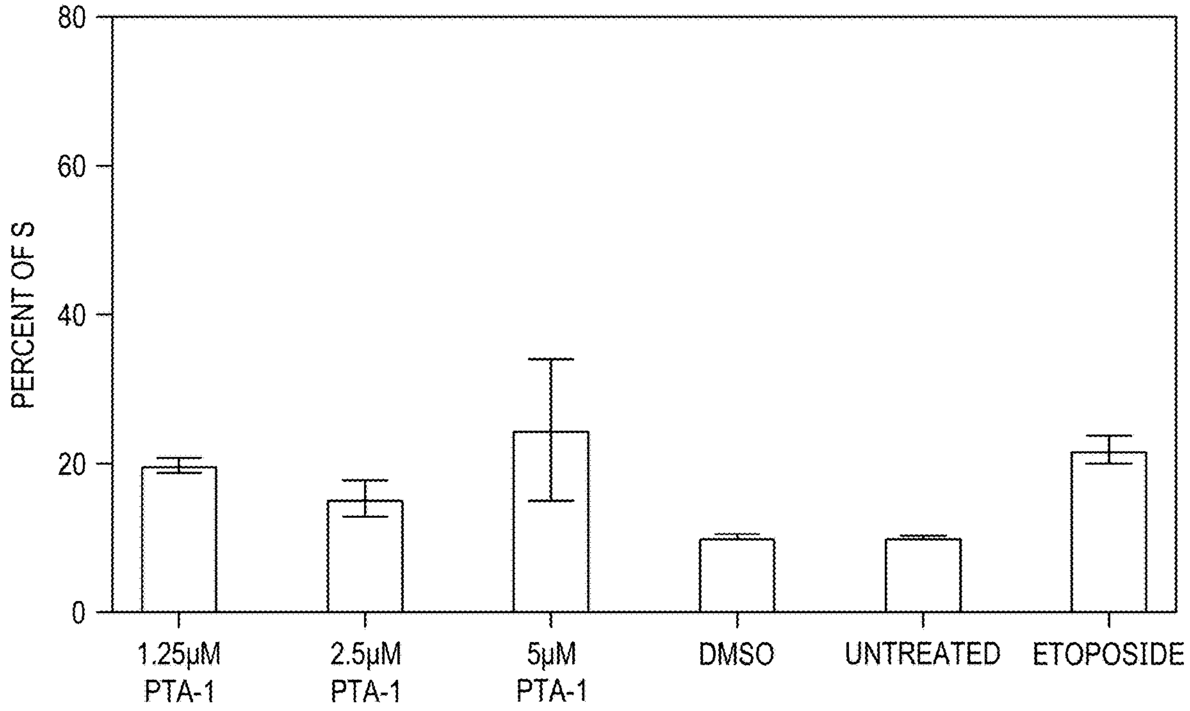
FIG. 5C illustrates PTA-1 induced arrest of cells in the S phase in accordance with an illustrative embodiment.

FIG. 5C illustrates PTA-1 induced arrest of cells in the S phase. As shown in FIG. 5C, treatment with PTA-1 at 1.25 μM, 2.5 μM, and 5 μM produces 19.8%, 15.34%, and 24.6% of the cells in the S phase, respectively. On the other hand, fewer cells are in the S phase after treatment with DMSO (10.2%) and without treatment (10.3%). In this example, FIG. 5C indicates that PTA-1 produces an arrest in the S phase in comparison to DMSO.

Figure 5D:
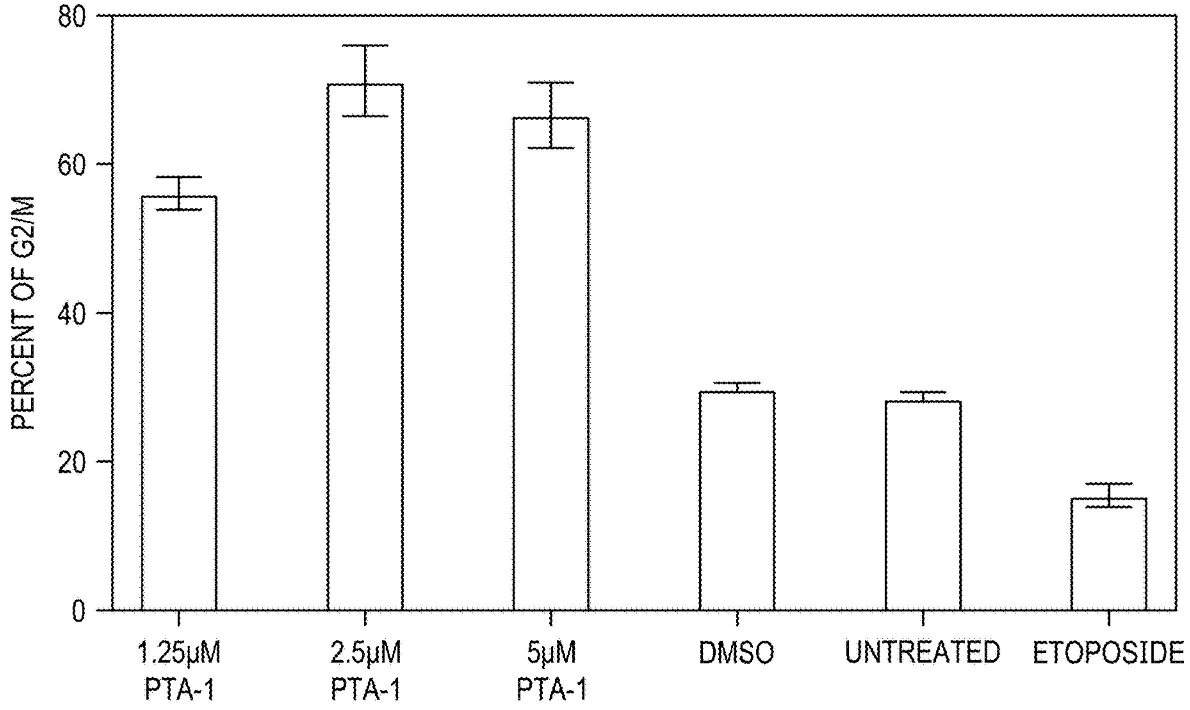
FIG. 5D illustrates PTA-1 induced arrest of cells in the G2/M phase in accordance with an illustrative embodiment.

FIG. 5D illustrates PTA-1 induced arrest of cells in the G2/M phase. In addition to the S phase, the percentages of cells treated with PTA-1 are higher than controls in the G2/M phase. As depicted in FIG. 5D, 53.25%, 71.5%, and 66.47% of cells are in the G2/M phase after treatment with 1.25 μM, 2.5 μM, and 5 μM of PTA-1, respectively. On the other hand, 29.86% of the cells are in the G2/M phase after being treated with DMSO, and 15.4% of the cells are in the G2/M phase after being treated with etoposide. In addition, 28.78% of untreated cells were in the G2/M phase.

In this example, results in FIG. 5C and FIG. 5D indicate that PTA-1 arrests the cell cycle in the S phase and the G2/M phase since higher percentages of cells in the G2/M phase are shown. Such observations suggest that PTA-1 favorably arrests the cell cycle in the G2/M phase which is where tubulin inhibitors affect the cell cycle. In this example, PTA-1 could be interfering with the mitotic complex and the mitotic spindle formed during G2/M phase.

FIG. 6 depicts a table of genes regulated by PTA-1 in accordance with an illustrative embodiment. In FIG. 6, PTA-1 treated MDA-MB-231 cells reveal a total of 116 genes that are significantly up-regulated, and 87 genes that are down-regulated after 6 hours of treatment. In addition, 24 hours of exposure to PTA-1 shows a significant up-regulation of 198 genes and down-regulation of 532 genes. Further analyses revealed that 61 genes are upregulated, and 47 genes are downregulated in both times, as illustrated in table 600 in FIG. 6.

FIG. 7 illustrates a connectivity map of known cancer drugs. Connectivity map 700 is a repository of transcriptomic data related to gene expression of various cancer cell lines cell treated with existing drugs. In the present example, the drugs represented in connectivity map 700 are known tubulin inhibitors. Tubulin inhibitors are a class of compounds that interfere with tubulin and have become an efficient strategy to develop anti-cancer drugs.

To identify the potential target of the PTA-1 compounds, the differentially expressed genes from MDA-MB-231 cells treated with PTA-1 were compared with the connectivity map 700. In this example, columns 702 show the expression levels of genes in different cell lines when treated with existing drugs from column 704. The gene expression profile of overlapping genes of MDA-MB-231 cells after treatment with PTA-1 for 24 hours show that PTA-1 has a gene expression signature similar to that of known tubulin inhibitors in the eight cancer cell lines shown in FIG. 7. In other words, the similarity in gene expression demonstrated by PTA-1 with the known tubulin inhibitors shown in FIG. 7 indicates that PTA-1 is a tubulin polymerization inhibitor.

Figure 8:
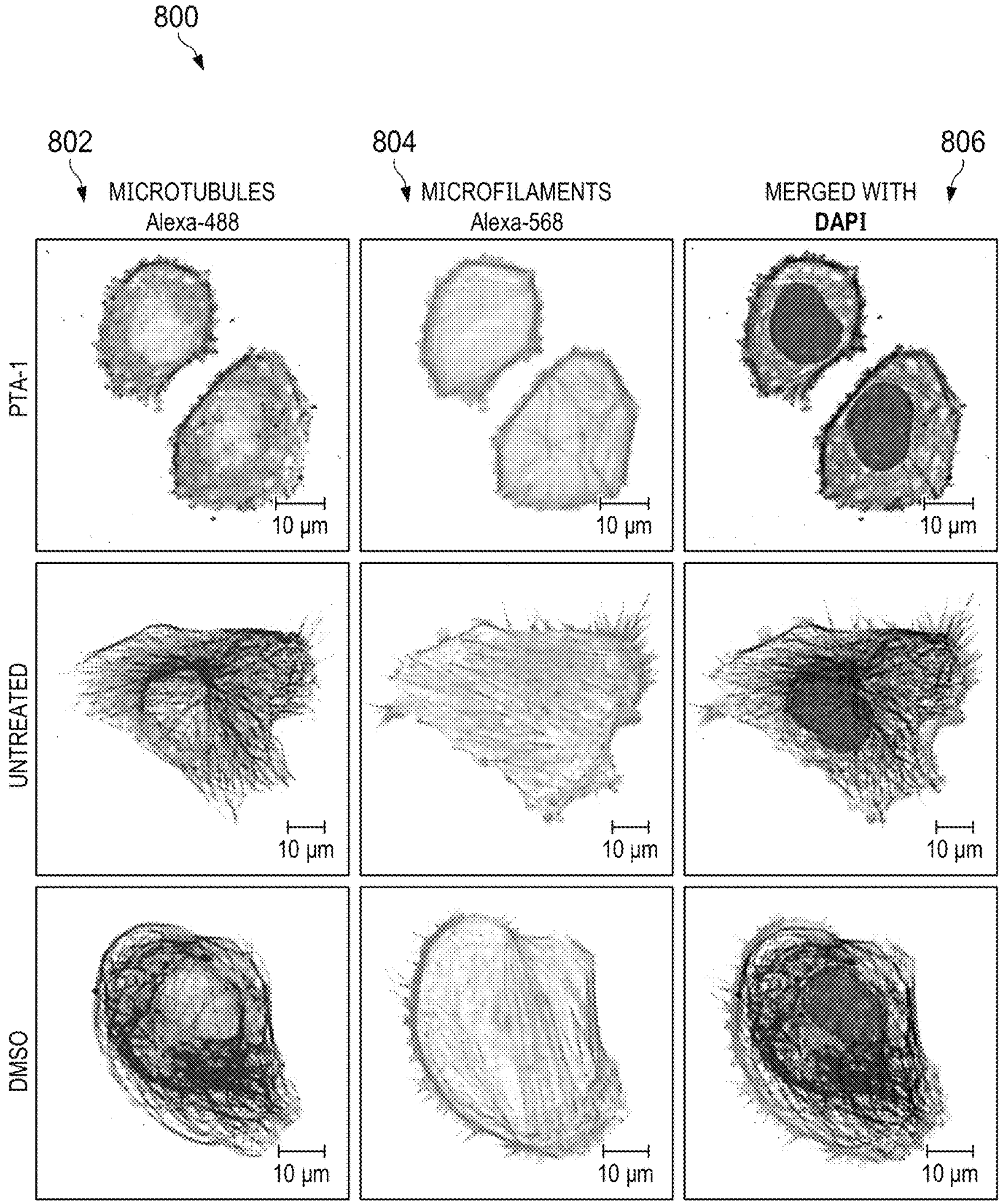
FIG. 8 illustrates alterations in cytoskeletal structures of MDA-MB-231 cells in response to treatment with PTA-1 in accordance with an illustrative embodiment.

FIG. 8 illustrates alterations in cytoskeletal structures of MDA-MB-231 cells in response to treatment with PTA-1 in accordance with an illustrative embodiment. To test the hypothesis that PTA-1 acts as a tubulin inhibitor, we tested if it could cause alterations in the microtubule organization of MDA-MB-231 cells.

Disruption of cellular microtubules of MDA-MB-231 cells can be assessed by imaging microtubules using fluorescence microscopy. In this illustrative example, column 802 shows the microtubule structures of cells treated with PTA-1, DMSO, and untreated cells using α-tubulin-Alexa-488 for staining. Column 804 shows the microfilament structures of cells treated with PTA-1, DMSO, and untreated cells using phalloidin-Alexa-568 for staining. Column 806 shows the merged images that also include nucleus of cells treated with PTA-1, DMSO, and untreated cells using 4' 6-diamidino-2-pheylindole (DAPI).

In this example, exposure of MDA-MB-231 cells to 10 μM of PTA-1 for 4 hours disrupts the microtubule organization since the tubular structure of the microtubules vanished. In other words, the tubulin in these cells is shapeless while the tubulin in cells treated with 1% DMSO and untreated cells looked normal, as shown in column 802. In contrast, the microfilament structure remained unaltered for all treated cells and the untreated cells, as shown in column 804. In summary, the treatment with PTA-1 causes spaces without tubulin while treatment with 1% of DMSO did not produce the disruption of the tubular structure of the microtubules. In addition, untreated cells keep an intact morphology after 4 hours.

These images indicate that PTA-1 alters microtubule organization in cells while producing no damage to the microfilaments. In this example, the effect of PTA-1 is observed just in the microtubules, suggesting that PTA-1 inhibits tubulin polymerization.

Figure 9:
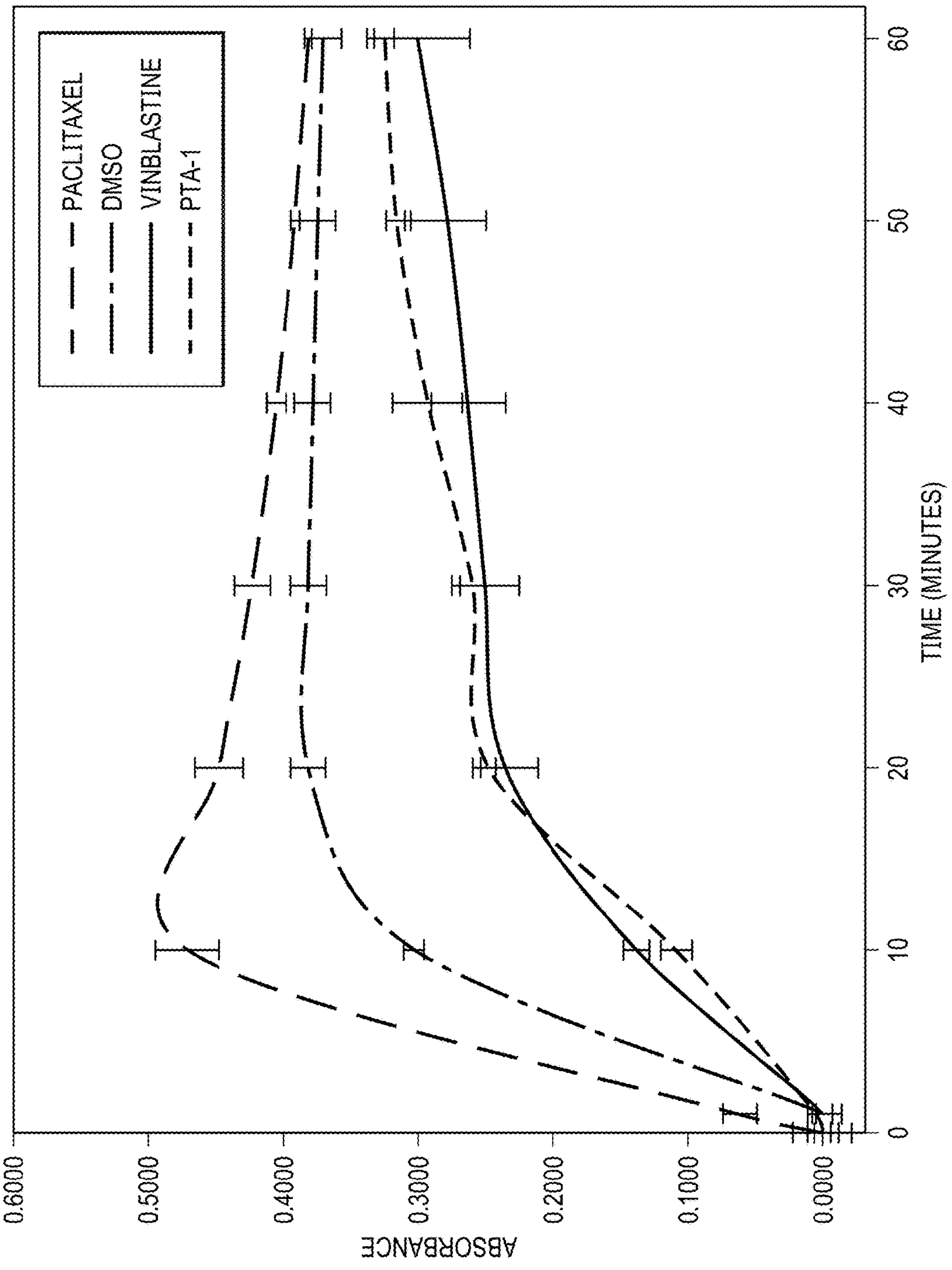
FIG. 9 depicts a graph illustrating tubulin polymerization of cells treated with PTA-1 in accordance with an illustrative embodiment.

FIG. 9 depicts a graph illustrating tubulin polymerization of cells treated with PTA-1 in accordance with an illustrative embodiment. Graph 900 illustrates the kinetic curves of four different treatments for tubulin polymerization.

In this illustrative example, absorbance is directly correlated with tubulin polymerization. Therefore, if polymerization happens, there is an increase in the absorbance at 340 nm. Expectedly, the growth phase of tubulin polymerization after treatment with paclitaxel (PTX) started immediately as expected as it is known to stabilize tubulin polymerization. In graph 900 tubulin polymerization can be clearly observed from the increasing absorbance after treatment with PTX. In this example, tubulin polymerization for cells treated with PTX drops immediately after 10 minutes.

Cells treated with DMSO, Vinblastine, and PTA-1 have an increasing level of absorbance starting after four minutes, which means that the nucleation phase lasted four minutes. However, cells treated with DMSO reach steady state after 14 minutes with an absorbance of 0.3662. In contrast, the steady state of cells treated with PTA-1 is reached after 20 minutes. After 60 minutes of treatment, cells treated with DMSO and cells treated with PTA-1 have significantly different absorbance values of 0.3702 and 0.3247, respectively.

In this example, cells treated with PTA-1 also produce a similar kinetic curve to cells treated with the well-known tubulin inhibitor Vinblastine. The kinetic curves for cells treated with PTA-1 and Vinblastine never reached the absorbance values of cells treated with DMSO. In graph 900, the kinetic curve for cells treated with PTA-1 indicates that PTA-1 can inhibit tubulin polymerization, therefore acting as a tubulin polymerization inhibitor for cancer therapy.

Figure 10A:
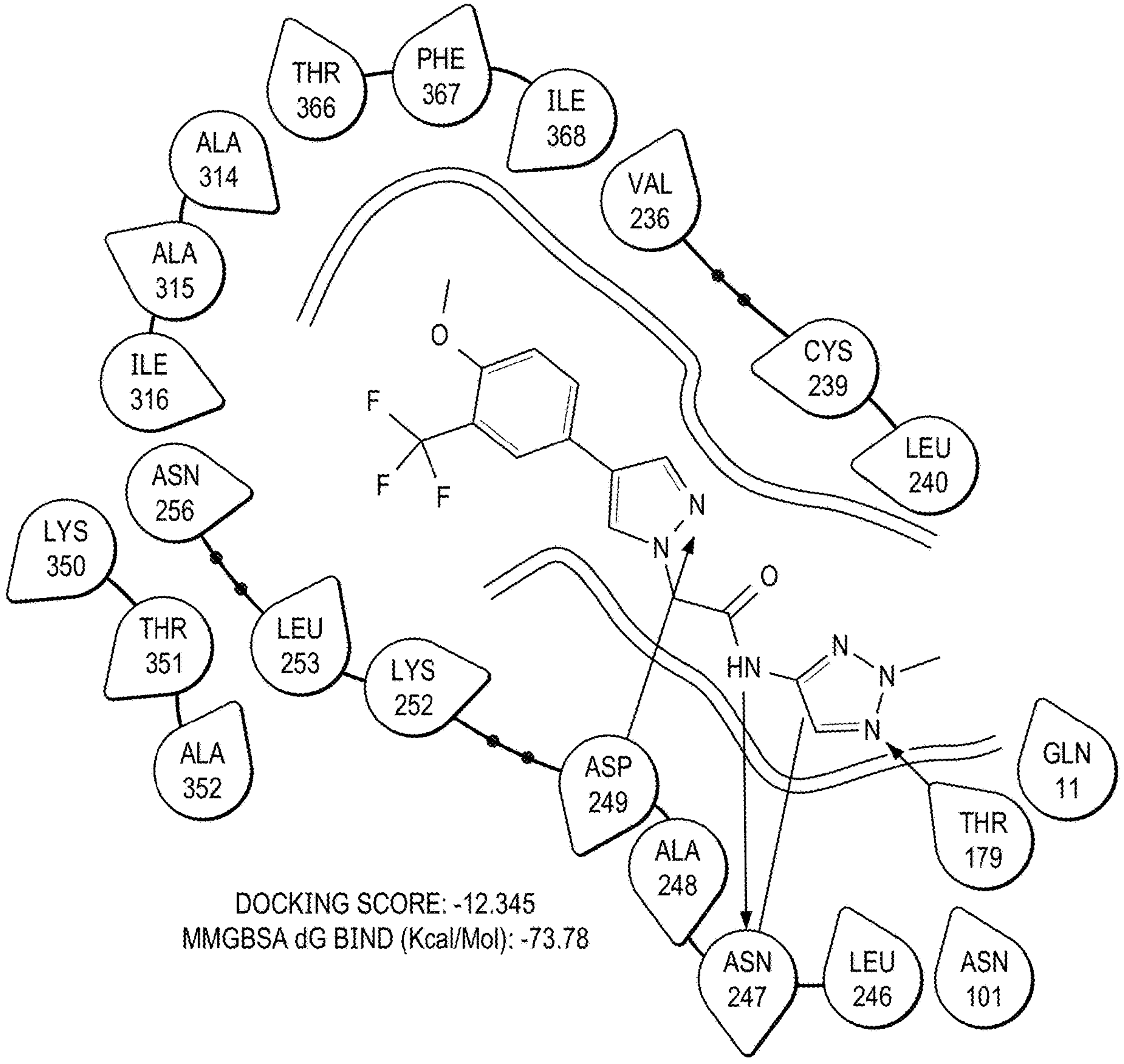
FIG. 10A illustrates a docking study for interaction of PTA-1 and tubulin.
Figure 10B:
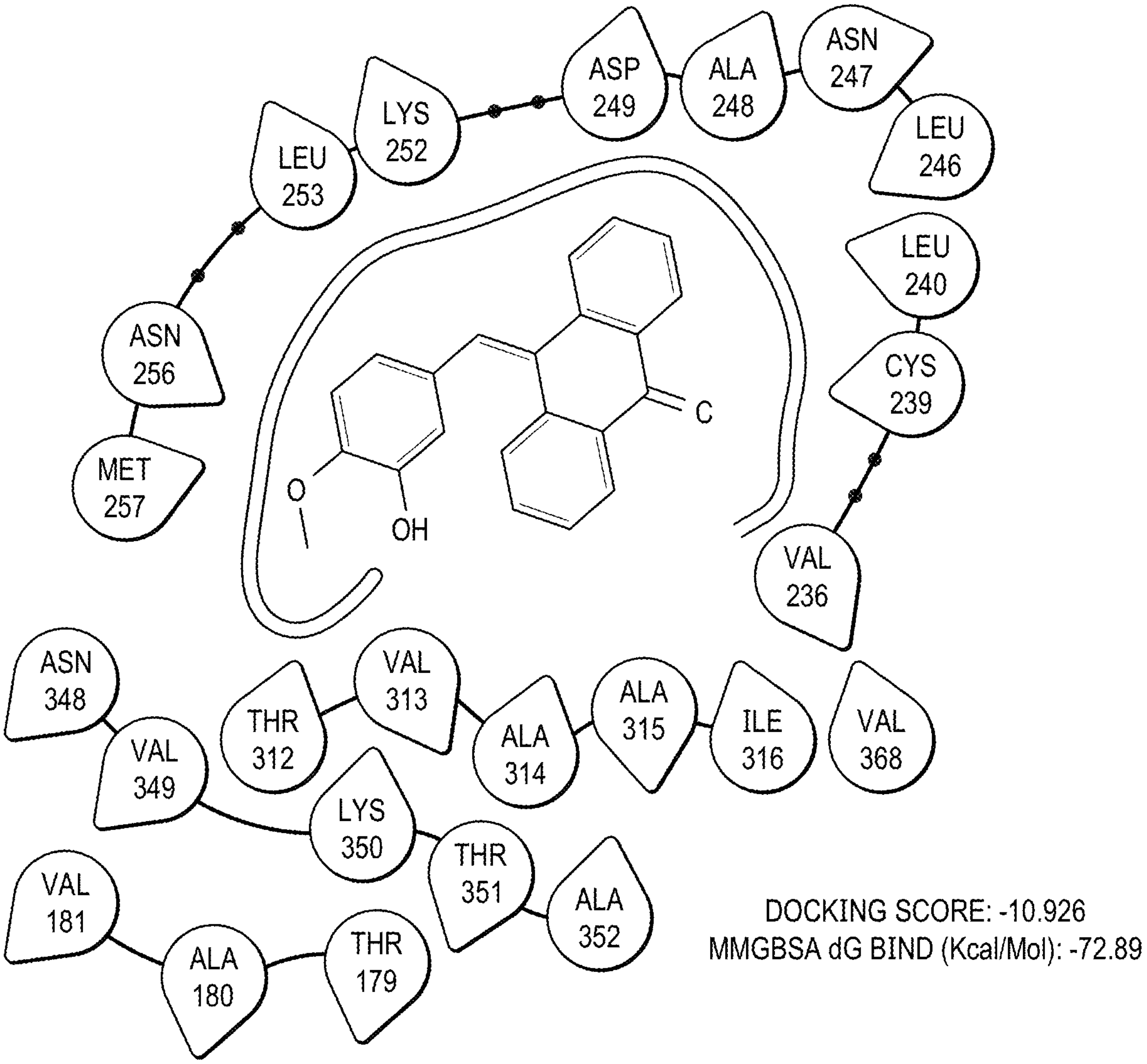
FIG. 10B illustrates a docking study for interaction between tubulin and 89U.

FIG. 10A illustrates a docking study for interaction of PTA-1 and tubulin. FIG. 10B illustrates a docking study for interaction between tubulin and 89U. A docking study is a type of computer-based analysis that predicts the interaction between molecules and output scores to represent the qualities of binding interactions. In this example, the docking study for interaction between PTA-1 and tubulin can be performed using Schrödinger software, AutoDock, FlexX, or any suitable computer software that can be used to predict interactions between molecules.

FIG. 10A shows that PTA-1 interacts well with tubulin since PTA-1 interacts mostly with hydrophobic residues on tubulin. In this example, the interaction between PTA-1 and tubulin has a docking score of −12.345. In contrast, FIG. 10B shows the interaction between tubulin with 89U. 89U is a known inhibitor that interacts with tubulin and can be used to crystalize tubulin protein. In FIG. 10B, the interaction between tubulin and 89U inhibitor has a docking score of −10.926. PTA-1 is shown to have capability to interact with tubulin since PTA-1 has a better (more negative) docking score compared to the 89U inhibitor when interacting with tubulin.

All of the methods disclosed and claimed herein can be made and executed without undue experimentation in light of the present disclosure. While the compositions and methods of the present disclosure have been described in terms of preferred embodiments, it will be apparent to those of skill in the art that variations may be applied to the methods and in the steps or in the sequence of steps of the method described herein without departing from the concept, spirit, and scope of the present disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the present disclosure as defined by the appended claims.

What is claimed is:

1. A method of inducing apoptosis of cancer cells, the method comprising administering the cancer cells with a compound comprising the chemical structure of 2-{4-[4-methoxy-3-(trifluoromethyl)phenyl]-1H-pyrazol-1-yl}-N-(2-methyl-2H-1,2,3-triazol-4-yl)acetamide.

2. A method of inhibiting tubulin polymerization of cancer cells, the method comprising administering the cancer cells with a compound comprising the chemical structure of 2-{4-[4-methoxy-3-(trifluoromethyl)phenyl]-1H-pyrazol-1-yl}-N-(2-methyl-2H-1,2,3-triazol-4-yl)acetamide.

* * * * *